United States Patent [19]
Harhen

[11] Patent Number: 5,876,329
[45] Date of Patent: *Mar. 2, 1999

[54] ENDOSCOPE WITH SHEATH RETAINING DEVICE

[75] Inventor: E. Paul Harhen, Duxbury, Mass.

[73] Assignee: Vision-Sciences, Inc., Natick, Mass.

[*] Notice: The term of this patent shall not extend beyond the expiration date of Pat. No. 5,685,822.

[21] Appl. No.: 922,417

[22] Filed: Sep. 3, 1997

Related U.S. Application Data

[63] Continuation of Ser. No. 694,924, Aug. 8, 1996, Pat. No. 5,685,822.

[51] Int. Cl.⁶ .................................................. A61B 1/04
[52] U.S. Cl. ........................... 600/125; 600/121; 600/129
[58] Field of Search .................................... 600/121, 122, 600/123, 124, 125, 129, 127, 186, 203; 604/263

[56] References Cited

U.S. PATENT DOCUMENTS

| Re. 34,110 | 10/1992 | Opie et al. ................................. | 128/6 |
| 4,646,722 | 3/1987 | Silverstein et al. ........................ | 128/4 |
| 4,815,470 | 3/1989 | Curtis et al. ....................... | 128/662.03 |
| 4,991,565 | 2/1991 | Takahashi et al. ........................... | 128/4 |
| 4,997,084 | 3/1991 | Opie et al. ............................... | 206/364 |
| 5,159,919 | 11/1992 | Chikama ..................................... | 128/4 |
| 5,193,525 | 3/1993 | Silverstein et al. ........................ | 128/4 |
| 5,201,908 | 4/1993 | Jones .......................................... | 128/4 |
| 5,257,617 | 11/1993 | Takahashi ............................... | 600/123 |
| 5,359,991 | 11/1994 | Takahashi et al. ....................... | 600/122 |
| 5,419,310 | 5/1995 | Frassica et al. ............................ | 128/4 |
| 5,477,148 | 12/1995 | Oneda et al. ............................ | 600/131 |
| 5,486,154 | 1/1996 | Kelleher .............................. | 600/129 X |
| 5,556,367 | 9/1996 | Yabe et al. .......................... | 600/121 X |
| 5,685,822 | 11/1997 | Harhen ................................. | 600/129 X |

Primary Examiner—Beverly M. Flanagan
Attorney, Agent, or Firm—Seed and Berry LLP

[57] ABSTRACT

An endoscope for use with an elastomeric sheath for performing an endoscopic procedure. The endoscope includes a body, an insertion tube extending away from the body and terminating at a distal end portion, and a sheath retainer connected to the distal end portion of the insertion tube for releasably retaining the sheath on the insertion tube in a substantially fixed position during the endoscopic procedure. The sheath is an elastomeric member movable between a radially expanded position and a contracted position, and the sheath is biased toward the contracted position. The sheath retainer is a generally C-shaped member having a pair of retaining tabs spaced apart from each other and extending away from an outer surface of the insertion tube's distal end portion to define a working channel retaining area therebetween. The retaining tabs are positioned and sized to engage a portion of the sheath at its distal end portion and to prevent the distal end portion of the sheath from moving axially relative to the distal end portion of the insertion tube, particularly during an endoscopic procedure.

13 Claims, 5 Drawing Sheets

ENDOSCOPE WITH SHEATH RETAINING DEVICE

CROSS-REFERENCE TO RELATED APPLICATION

This is a continuation application of U.S. application No. 08/694,924 filed Aug. 8, 1996, issued as U.S. Pat. No. 5,685,822.

TECHNICAL FIELD

This invention relates to endoscopy, and more particularly, to an endoscope assembly for isolation of an endoscope from contaminants during an endoscopic procedure.

BACKGROUND OF THE INVENTION

The use of endoscopes for diagnostic and therapeutic indications is rapidly expanding. To improve performance, endoscopes have been optimized to best accomplish their purpose. Therefore, there are upper endoscopes for examination of the esophagus, stomach, and duodenum, colonoscopes for examining the colon, angioscopes for examining blood vessels, bronchoscopes for examining the bronchi, laparoscopes for examining the peritoneal cavity, and arthroscopes for examining joint spaces. The discussion which follows will apply to all of these types of endoscopes.

Instruments to examine the rectum and sigmoid colon, known as flexible sigmoidoscopes, are good examples of the usefulness of this endoscopy technology. These devices are expensive, used in contaminated environments for a procedure which is brief (5–10 minutes), and where problems of cleaning time and contamination are important factors. There has been a large increase in the use of the "flexible sigmoidoscope" for use in screening symptomatic and asymptomatic patients for colon and rectal cancer. Ideally, flexible sigmoidoscopes must be used frequently and inexpensively in order to maintain the cost of such screening at acceptable levels. Typically, a clinic would like to perform five to ten sigmoidoscope examinations each hour. One significant problem with making such frequency of examinations inexpensive is the time necessary for adequately cleaning the device. While external surfaces of endoscopes can be adequately cleaned, endoscopes typically have air, water, biopsy, and suction channels extending along their length which come into contact with bodily tissues or fluid. It is extremely difficult to adequately clean these channels even when skilled health practitioners spend a great deal of time on the cleaning procedures. Accordingly, conventional endoscope cleaning techniques greatly increase the cost of endoscopic procedures.

One approach to the endoscope contamination problem is described and claimed in U.S. Pat. No. 4,646,722 to Silverstein et al. The Silverstein et al. patent discloses the use of a flexible elastomeric sheath that surrounds the insertion tube of an endoscope. The distal end portion of the sheath includes a transparent window that covers a viewing window at the distal end portion of the insertion tube. The sheath also includes one or more channels that extend through the sheath adjacent to the insertion tube to allow endoscopic procedures to be performed without contaminating the endoscope itself. Once a procedure has been completed, the sheath, including its channels, is removed from the endoscope thus leaving the endoscope free to perform additional procedures without cleaning or disinfecting. The approach described in the Silverstein et al. patent has provided a great improvement in the ability to efficiently conduct endoscopic procedures without either the risk of contamination or the expense of a thorough cleaning and disinfecting between the procedures.

Traditional endoscopes have an insertion tube constructed of a vinyl or urethane covered spring connected to an articulating section comprised of metal vertebrae covered with a rubber material. This insertion tube construction gives the required axial and torsional rigidity for most of the length of the endoscope along with a more flexible articulating section which can be moved with little applied force in a relatively tight bending radius. The placement of a tight fitting sheath surrounding the insertion tube, although it is needed for the length of the insertion tube, can detrimentally inhibit mobility, control, and flexibility at the articulating section.

Installation and retention of the sheath on the endoscope are important procedures that must be completed with care to ensure that the distal end portion of the insertion tube is properly positioned at the distal end portion of the sheath for proper visibility through the window at the distal end portion of the endoscope. Sheaths have been installed on endoscopes using an inflation procedure, as is taught in U.S. Pat. No. 5,419,310, wherein the elastomeric sheath is inflated to an expanded position, and the endoscope's insertion tube is inserted into the sheath. After the insertion tube is properly positioned in the sheath, the sheath is deflated so that it contracts onto the insertion tube. A problem with the use of a flexible elastomeric sheath, such as latex, is that longitudinal as well as radial expansion of the sheath occurs upon inflation, and such expansion can leave a loose or baggy distal end portion as the sheath deflates, particularly if it deflates toward the proximal end portion first. The baggy distal end portion of the sheath is a problem because the transparent window in the sheath's distal end portion can be easily improperly positioned relative to the endoscope's viewing window, which can result in glare and poor visibility.

A further drawback and problem encountered during installation of the insertion tube into the sheath is ensuring a secure connection between the distal tip of the endoscope and the distal tip of the sheath. Differential lengths of the sheath as compared to the insertion tube have been used to keep the distal end portions of the scope and sheath in adjacent proximity by stretching the sheath so as to pull the distal end portion of the sheath against the distal end portion of the tip. This procedure of using differential lengths is known as preloading. However, preloading is typically not satisfactory when the sheath includes working channel for the passage of endoscopic accessories or other instrumentation. The force required to pass a tool through the working channel, particularly when the channel is bent about a tight radius, is sometimes sufficient to dislodge the distal tip of the sheath from the distal tip of the insertion tube. Thus, the viewing window in the sheath is displaced from the distal end portion of the insertion tube and causes glare or focus problems at the imaging lens in the insertion tube's distal end portion.

Another drawback of preloading is an increase in the force required to articulate the endoscope due to additionally stretching the already preloaded elastomer employed in the sheath construction. U.S. Pat. No. 5,477,148 teaches the use of an endoscope with a sheath having an end cap that engages the distal-end portion of the endoscope's insertion tube with seal members that provide a detent engaging the insertion tube. These detents ensure that the distal tip of the sheath and the distal end portion of the insertion tube remain locked together during the endoscopic procedure. In addition, the force required to articulate the sheathed insertion tube is reduced, because installation of the sheath requires less stretching and reduced preloading for retention of the sheath on the insertion tube.

However, the drawback of utilizing these detents is that the distal end portion of the sheath must be manually installed and removed. Generally, some level of expertise is required to successfully execute the installation and removal procedure. In addition, the unsnapping of the sheath's distal end portion from the insertion tube typically requires that a contaminated distal end portion of the endoscope be grasped by a user to disengage the sheath, often resulting in contamination of the user's hand(s). Such contamination of the user's hand(s) is then problematic, due to the risk of the user contaminating other instrumentation, equipment, personnel, or the like.

SUMMARY OF THE INVENTION

The present invention provides an endoscope with an insertion tube coverable by a resilient sheath having a working channel extending therethrough that overcomes the problems experienced by conventional endoscope systems. In a preferred embodiment of the invention, the endoscope has a handle and an insertion tube connected at its proximal end portion to the handle. The insertion tube has a non-circular cross-sectional area and an outer surface defined by first and second portions, the first portion being semi-cylindrical. A sheath retaining member is attached to the insertion tube's distal end portion. The sheath retaining member has a pair of spaced-apart retaining tabs protruding away from the distal end portion of the insertion tube. The retaining tabs define a working channel receiving area therebetween adjacent the second portion of the insertion tube's outer surface. The retaining tabs are to be securely and tightly surrounded by the sheath to hold the distal end portion of the sheath in a fixed position relative to the distal end portion of the insertion tube.

The retaining tabs are sized and positioned so the distal end portion of the sheath is stretched over the retaining tabs when the distal end portion of the insertion tube is adjacent the distal end portion of the sheath and when the distal end portion of the sheath is in the contracted position. The retaining tabs have engaging surfaces that engage the sheath when the sheath is in the contracted position and prevent axial movement of the sheath's distal end portion relative to the insertion tube's distal end portion, particularly during an endoscopic procedure.

In the preferred embodiment of the present invention, the distal end portion of the insertion tube has a head extending distally from a flexible articulation system. The head and the flexible articulation system each have generally D-shaped cross-sectional areas, and the cross-sectional area of the head is smaller than the cross-sectional area of the flexible articulation system. The sheath retainer is generally a C-shaped member with two free ends that define the sheath retaining tabs. The curved body of the C-shaped sheath retainer is connected to the head adjacent to the flexible articulation system.

The present invention also provides a method of installing the endoscopic insertion tube into the endoscopic sheath to securely retain the distal end portion of the insertion tube adjacent to the distal end portion of the sheath. The method includes radially expanding the sheath from a contracted position to an expanded position. In the expanded position, the sheath is sized to receive the endoscope insertion tube therein with minimal interference. The insertion tube is then inserted into the sheath, and the distal end portion of the insertion tube is positioned with the sheath retaining member thereon adjacent to the distal end portion of the sheath. The sheath is moved from the expanded position to the contracted position after the distal end portion of the insertion tube is adjacent to the distal end portion of the sheath, and a portion of the sheath is stretched over the sheath retaining member with the stretched portion of the sheath exerting a compressive force on the sheath retaining member. The sheath retaining member engages and retains the distal end portion of the sheath adjacent to the distal end portion of the insertion tube and prevents axial movement of the distal end portion of the sheath relative to the insertion tube.

DETAILED DESCRIPTION OF THE INVENTION

Figure 1:
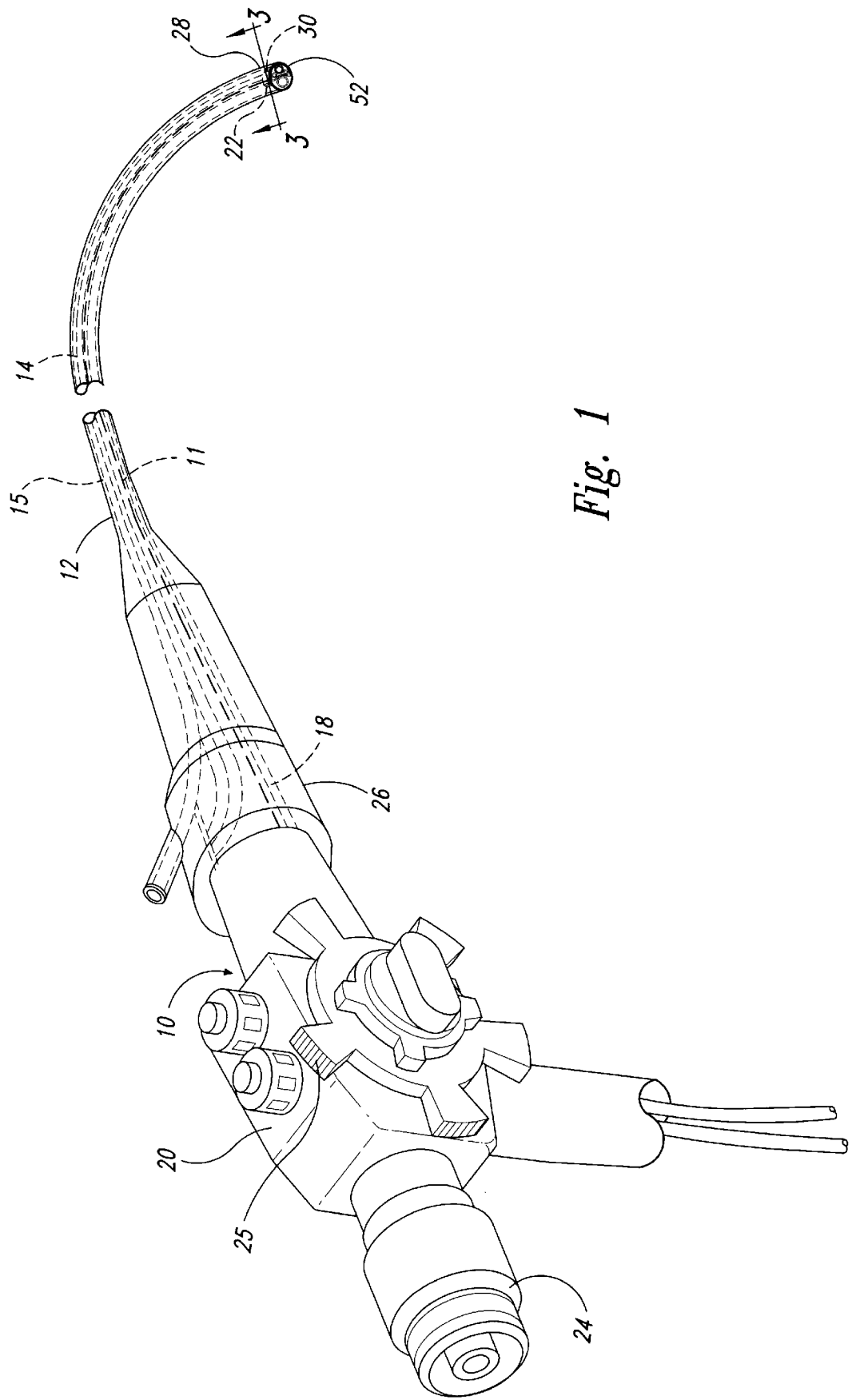
FIG. 1 is an isometric view of an endoscopic sheath installed on an endoscope having an insertion tube in accordance with the present invention.

A preferred embodiment of the invention is described herein and shown in the attached drawings for illustrative purposes. As best seen in FIG. 1, an endoscope 10 having an elongated, flexible insertion tube 11 in accordance with the present invention is used with a protective sheath 12 for therapeutic or diagnostic endoscopic procedures. The insertion tube 11 connects at its proximal end portion 18 to a handle 20 and extends from the handle to a distal end portion 22. The distal end portion 22 of the insertion tube 11 has a sheath retainer 30 thereon that engages the sheath 12 and securely retains a distal end portion 28 of the sheath adjacent to the distal end portion of the insertion tube.

The sheath assembly 12 has a proximal end portion 26 that surrounds the proximal end portion 18 of the insertion tube 11 when installed in the sheath, and a distal end portion 28 that surrounds the distal end portion 22 of the insertion tube. The sheath 12 is made of a flexible, thin, resilient elastomeric material such as latex, that defines an endoscope tube 15 sized to removably receive the insertion tube 11 so the sheath fits over and snugly surrounds the insertion tube. The sheath 12 isolates the endoscope's insertion tube 11 while creating a negligible resistance to bending of the insertion tube, particularly its distal end portion 22, during the endoscopic procedure. The sheath 12 includes a working channel 14, such as a biopsy channel or the like, extending through the sheath 12 along the length of the insertion tube 11. The distal end portion 28 of the sheath 12 is sealed except for an opening into the working channel 14, so the insertion tube 11 is completely isolated from contaminants.

The sheath retainer 30 on the distal end portion 22 of the insertion tube 11 is shaped and sized such that, when the sheath 12 is fully installed on the insertion tube, a portion of the sheath's distal end portion 28 is tightly stretched over the sheath retainer 30. Thus, the portion of the sheath 12 exerts a compressive force on the sheath retainer 30 such that the sheath retainer securely engages the sheath and prevents the distal end portion 28 of the sheath from moving axially relative to the distal end portion 22 of the insertion tube 11.

Figure 2:
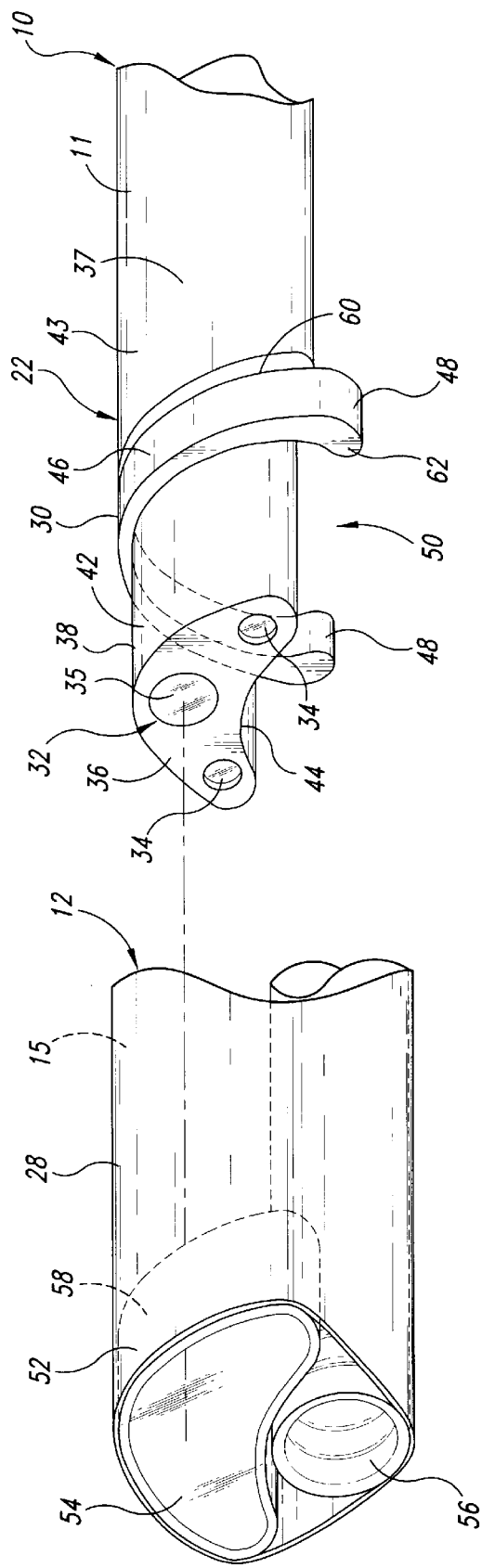
FIG. 2 is an enlarged, partially exploded isometric view of the distal end portion of the insertion tube and the distal end portion of the sheath of FIG. 1.

With further reference to FIG. 2, in the preferred embodiment, the insertion tube 11 contains a conventional imaging device 32 and lights or other illumination sources 34 for conveying an image from the distal end portion 22 of the insertion tube to an eye piece 24 connected to the handle 20. In the preferred embodiment, the imaging system 32 terminates at its distal end portion at a viewing window 35 that forms a portion of a distal end surface 36 of the insertion tube 11. If the distal end portion 28 of the sheath 12 is not securely held immediately adjacent to the viewing window 35 of the insertion tube II or if the distal end portion of the sheath is moved axially away from the viewing window, glare or other vision impairment can occur, thereby detrimentally affecting the physician's view obtained from the imaging device 32. Control wires located in the insertion tube 11 are connected to the distal end portion 22 and to control wheels 25 mounted on the handle 20. The control wheels 25 and control wires allow a physician to move the distal end portion 22 of the insertion tube left, right, up, down or any combination thereof, so the insertion tube 11 will bend about its neutral bending plane. The distal end portion 22 of the insertion tube 11 is sufficiently flexible to be articulated through short radius corners corresponding to contours of a body cavity so the physician can get a good look at the areas of the body cavity during the endoscopic procedure.

As best seen in FIG. 2, the distal end portion 22 of the insertion tube 11 is made up of a head 38 and a flexible articulation system 37. The head 38 extends proximally from the distal end surface 36 and connects to the flexible articulation system 37, and the flexible articulation system extends toward the insertion tube's proximal end portion. Each of the head 38 and the flexible articulation section 37 has a generally D-shaped cross-sectional area. The flexible articulation system 37 has a larger cross-sectional area than the head 38, so a shoulder 40 is formed at the intersection between the head and the flexible articulation system.

The head 38 has a semi-cylindrical curved top surface 42 with a radius that is smaller than the radius of a curved top surface 43 of the flexible articulation system 37. In the preferred embodiment, the head 38 and the flexible articulation section 37 each have an under surface 44 with a slight arcuate shape defining a groove along the under surface 44 of the insertion tube 11. The arcuate under surface 44 is shaped to receive and position a portion of the working channel 14 therein when the insertion tube 11 is inserted into the sheath 12.

The sheath retainer 30 is a C-shaped member fixedly connected to the head 38 immediately adjacent to the flexible articulation system 37 at the shoulder 40. The sheath retainer 30 has a curved body portion 46 connected to two free ends. The sheath retainer 30 is saddled onto the head 38 with the curved body portion 46 extending over and being securely connected to the curved top surface 42 of the head. The free ends of the sheath retainer 30 project away from the head 38 so as to form a pair of spaced-apart protruding retaining tabs 48 below the arcuate under surface 44 of the head. The retaining tabs 48 are spaced apart from each other to define an intermediate space 50 therebetween that is sized to receive at least a portion of the working channel 14 when the sheath 12 is installed on the insertion tube 11.

The curved body portion 46 of the sheath retainer 30 has an outer radius that is approximately equal to or slightly less than the radius of the curved top surface 43 of the flexible articulation system 37. The sheath retainer 30 is shaped and sized so it minimizes any increase in the cross-sectional area of the sheathed insertion tube 11 so as to minimize discomfort for a patient during or following the endoscopic procedure.

In the preferred embodiment, the curved body portion 46 of the sheath retainer 30 is integrally connected to the head 38 immediately adjacent to the shoulder 40. In alternate embodiments of the present invention, the sheath retainer 30 is fixed with a suitable adhesive or the like to the head 38 and can be replaced as needed due to wear, or for maintenance.

As best seen in FIG. 2, the distal end portion 28 of the sheath 12 includes a cap 52 that is sealably connected to the sidewalls of the sheath. The cap 52 has sidewalls 58 connected to a transparent end wall that is a viewing window 54 at the distal end portion 28 of the sheath 12. The cap 52 is shaped and sized to removably receive a distal portion of the head 38 so the viewing window 35 of the imaging system 32 is positioned immediately adjacent to the cap's viewing window 54 when the sheath 12 is properly installed on the insertion tube 11.

The cap 52 has a generally D-shaped cross-sectional area and the sidewalls 58 extend over a portion of the head 38 and terminate adjacent to the sheath retainer 30 so the sheath retainer is between the sidewalls and the shoulder 40. When the insertion tube 11 is properly positioned in the sheath 12, the cap 52, the sheath retainer 30, and the flexible articulation system 37 are sequentially aligned with the working channel 14 extending under all of them so the cross-sectional area along the distal end portion of the sheathed endoscope assembly is substantially constant, or in one embodiment slightly tapered, in the distal direction. This substantially constant or slightly tapering cross-sectional area is sized to minimize the discomfort experienced by a patient during a procedure while ensuring the sheath retainer 30 securely holds the distal end portion 28 of the sheath 12 in place.

Figure 3:
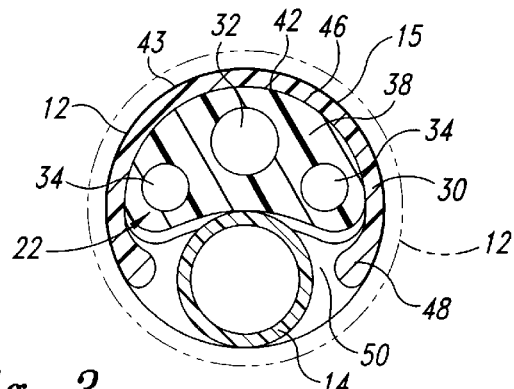
FIG. 3 is an enlarged cross-sectional view taken substantially along Line 3—3 of FIG. 1 showing the sheath in solid in a contracted position and showing the sheath in phantom in a radially expanded position.
Figure 4:
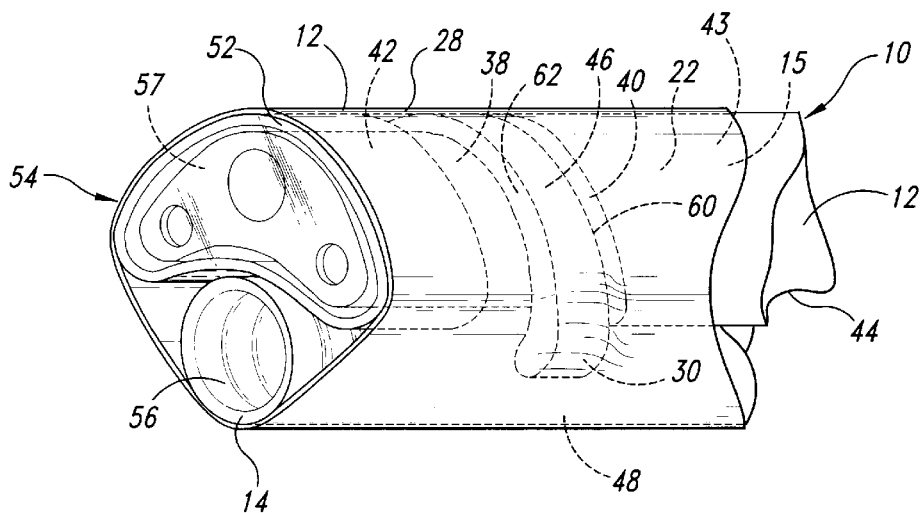
FIG. 4 is an enlarged isometric view of the distal end portion of the insertion tube and the distal end portion of the sheath of FIG. 1.

As best seen in FIGS. 3 and 4, the latex sheath 12 is a resiliently expandable member movable between a radially expanded position, shown in phantom in FIG. 3, and a contracted position, shown in solid. The sheath 12 is moved to the expanded position, for example, by conventional inflation or vacuum expansion techniques. When the sheath 12 is in the radially expanded position, the endoscope tube 15 of the sheath has an interior diameter large enough to easily receive the insertion tube 11, distal end portion 22 first, without excessive interference from the sheath retainer 30 for quick and accurate positioning of the insertion tube in the sheath. As the insertion tube 11 approaches the installed position, the cap 52 receives the distal end portion 22 and provides additional guidance for proper positioning of the head 38 and its viewing window 35 relative to the cap's viewing window 54.

After the insertion tube 11 is properly positioned in the sheath, the sheath is allowed to contract. As the sheath approaches the contracted position, a portion of latex sheath stretches around the sheath retainer 30 and tightly contracts over the curved body portion 46 and the free ends 48. The portion of the sheath 12 also extends over proximal and distal surfaces 60 and 62 of the retaining member 30. The portion of the sheath 12 tightly stretched over the sheath retainer 30 exerts a compressive force thereon. Accordingly, the distal end portion 28 of the sheath 12 frictionally engages the sheath retainer 30 and substantially restrains axial movement of the sheath's distal end portion relative to the insertion tube 11, particularly during an endoscopic procedure when an endoscopic tool is passed through the working channel 14.

In the preferred embodiment, the engagement between the sheath retainer 30 and the sheath 12 is sufficient to securely hold the distal end portion 28 of the sheath in place, and the rest of the sheath extending along the insertion tube 11 does not exert an excessive compressive force on the insertion tube that would inhibit articulation or control of the insertion tube. When the portion of the sheath 12 is stretched around the sheath retainer 30, the portion of the sheath also exerts a radially compressive force on the working channel 14 to hold the working channel against the arcuate under surface 44 of the insertion tube 11 between the free ends 48 of the sheath retainer 30. The sheath retainer 30 thus facilitates in retaining the working channel 14 in a selected position relative to the distal end portion 22 of the insertion tube 11 during the endoscopic procedure. The compressive force, however, is not sufficient to crush or kink the working channel 14.

As discussed above, the cap 52 in the sheath 12 facilitates in the proper positioning of the distal end portion 22 of the insertion tube 11 within the sheath. In one embodiment of the invention, the sheath retainer 30 is attached to the head 38 so the distal surface 62 of the sheath retainer abuts the sidewalls of the cap 52. Accordingly, the distance between the viewing window 54 in the cap 52 and the viewing window 35 of the head 38 can be very accurately controlled.

Figure 5:
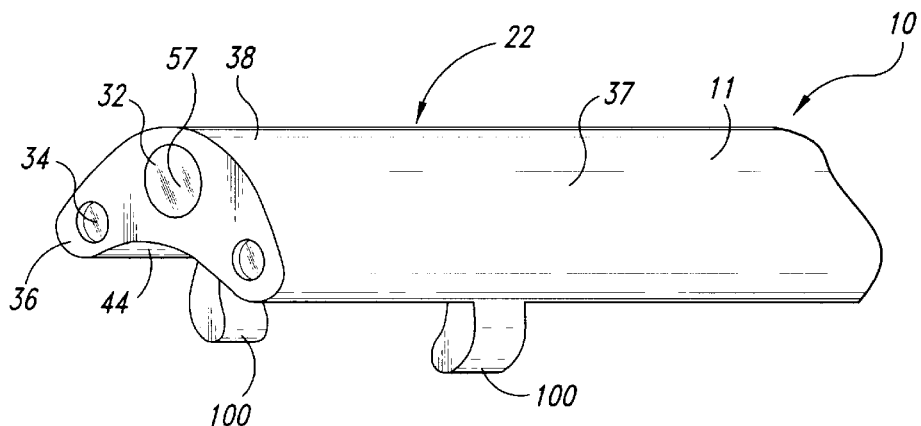
FIG. 5 is an isometric view of a distal end portion of an endoscope insertion tube of an alternate embodiment of the present invention.

In an alternate embodiment of the invention, as best seen in FIG. 5, a distal end portion 22 of the insertion tube 11 has a pair of rigid tabs 100 spaced apart from each other and extending away from the arcuate underside 44 of the head 38. The head 38 and the flexible articulation system 37 have substantially the same shape and cross-sectional area providing a smooth transition therebetween. The tabs 100 are integrally connected to the arcuate underside 44 of the head 38 and provide the intermediate space 50 sized to receive at least a portion of the working channel 14. The tabs 100 are shaped and sized to securely engage the sheath 12 to prevent movement of the distal end portion 28 of the sheath relative to the distal end portion 22 of the insertion tube 11.

Figure 6:
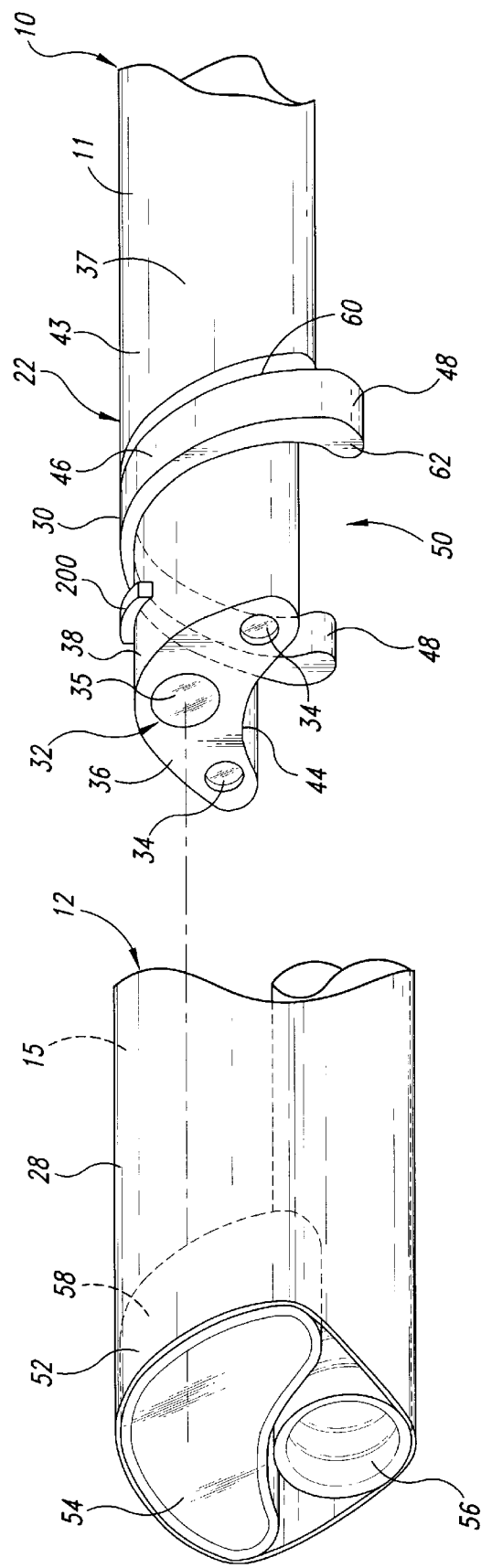
FIG. 6 is an enlarged, partially exploded isometric view of the distal end portion of the insertion tube of an alternate embodiment of the present invention.

In another alternate embodiment of the invention illustrated in FIG. 6, the head 38 of the insertion tube 11 includes a stop 200 projecting outwardly from the head at a selected location so the stop abuts the cap 52 in the sheath 12 when the insertion tube is fully installed in the sheath. The stop 200 works with the sheath retainer 30 to ensure that proper positioning of the insertion tube's distal end portion 22 relative to the sheath's distal end portion 28 is maintained during the endoscopic procedure.

Figure 7:
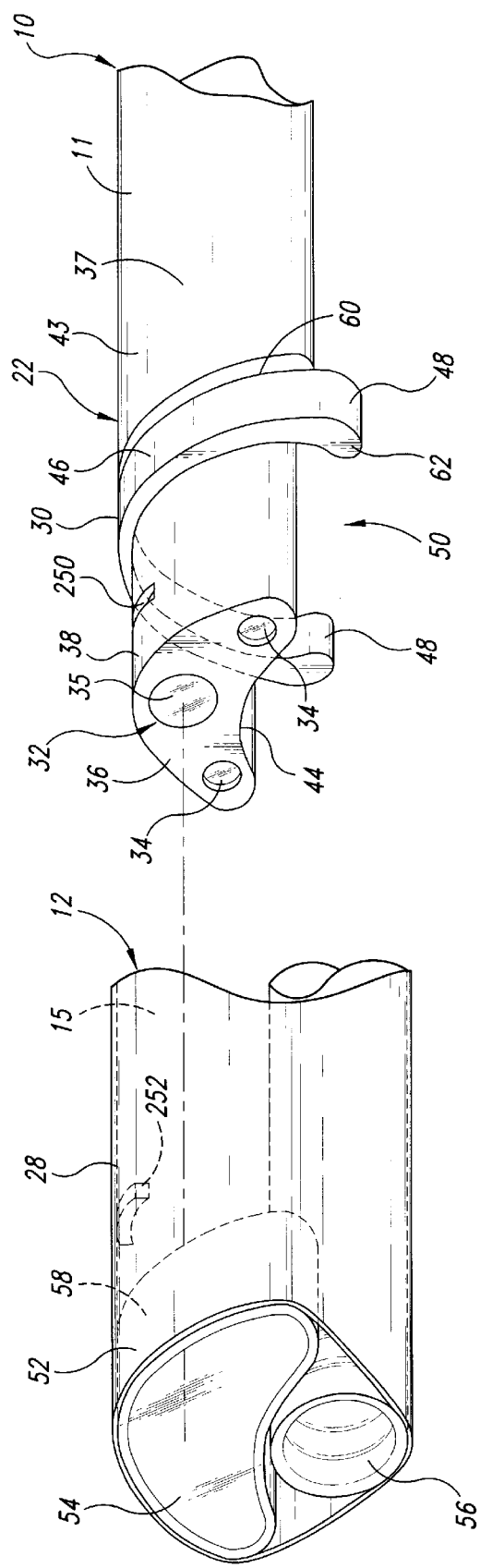
FIG. 7 is an enlarged, partially exploded isometric view of the distal end portion of the insertion tube of an alternate embodiment of the present invention.

In another embodiment of the present invention illustrated in FIG. 7, the distal end portion 22 of the insertion tube 11 has a recessed detail 250 therein that is shaped and sized to removably receive a retaining projection 252 integrally connected to the sheath 12 when the insertion tube 11 is fully inserted into the sheath. The retaining projection 252 extends radially inwardly into the endoscope tube 15 from the sheath's sidewalls, and when the sheath 12 is in the expanded position during installation of the insertion tube 11, the retaining projection is out of engagement with the insertion tube. When the distal end portion 22 of the insertion tube 11 is in position at the distal end portion 28 of the sheath 12 and the sheath is moved to the contracted position, the retaining projection 252 is inserted into the recessed detail 250 in the insertion tube's distal end portion 22. The retaining projection 252 retains the distal end portion 28 of the sheath 12 in a selected position and resists movement of the sheath's distal end portion during an endoscopic procedure. The retaining projection also works with the sheath retainer 30 discussed above to prevent axial movement of the sheath's distal end portion 28 relative to the distal end portion 22 of the insertion tube 11 during the endoscopic procedure, particularly during the passage of an endoscopic tool through the working channel 14.

Numerous modifications and variations of the endoscope with a sheath retaining device invention disclosed herein will occur to those skilled in the art in view of this disclosure. For example, the sheath retainer could be constructed to removably receive multiple working channels extending through the sheath. Therefore, it is to be understood that these modifications and variations, and equivalents thereof, may be practiced while remaining within the spirit and scope of the invention as defined in the following claims.

what is claimed is:

1. An endoscope for use with a sheath for performing an endoscopic procedure, the sheath having a distal end portion movable between a radially expanded position and a contracted position, the distal end portion of the sheath being biased toward the contracted position comprising:
   a handle;
   an insertion tube extending away from the handle portion and terminating at a distal end portion, the distal end portion of the insertion tube having a non-circular cross-sectional area and having a generally axially extending outer surface the insertion tube being removably coverable by the distal end portion of the sheath and insertable therein when the sheath is in the radially expanded position; and
   a sheath retaining member connected to the distal end portion of the insertion tube, the sheath retaining member having a pair of spaced-apart retaining tabs extending generally radially away from the outer surface of the distal end portion, the retaining tabs being sized so the distal end portion of the sheath is stretched over the retaining tabs when the distal end portion of the insertion tube is adjacent to the distal end portion of the sheath and when the distal end portion of the sheath is in the contracted position, the retaining tabs having engaging surfaces that engage the sheath when the sheath is in the contracted position and prevent the distal end portion of the sheath from moving axially relative to the distal end portion of the insertion tube.

2. The endoscope of claim 1 wherein the distal end portion of the insertion tube has a generally D-shaped cross-sectional area, and the sheath retaining member has a generally C-shaped cross-sectional area.

3. The endoscope of claim 1 wherein the distal end portion of the insertion tube has a shoulder portion and the sheath retaining member is adjacent to the shoulder portion on a distal side of the shoulder portion.

4. The endoscope of claim 1 wherein the retaining tabs are integrally connected to the insertion tube.

5. An endoscope assembly for performing an endoscopic procedure, comprising:

a sheath having a distal end portion movable between a radially expanded position and a contracted position, the distal end portion of the sheath being biased toward the contracted position; and an endoscope having an insertion tube terminating at a distal end portion, and a sheath retaining member connected to the distal end portion of the insertion tube, the distal end portion of the insertion tube having a generally axially extending outer surface the sheath retaining member having a pair of spaced-apart retaining tabs extending generally radially away from the outer surface of the distal end portion of the insertion tube the retaining tabs being sized so the distal end portion of the sheath is stretched over the retaining tabs when the distal end portion of the insertion tube is adjacent the distal end portion of the sheath and when the distal end portion of the sheath is in the contracted position, the retaining tabs having engaging surfaces that engage the sheath when the sheath is in the contracted position and that prevent the distal end portion of the sheath of the insertion tube from moving relative to the distal end portion of the insertion tube.

6. The endoscope assembly of claim 5 wherein the distal end portion of the insertion tube has a shoulder portion thereon, the sheath retaining member being attached to the insertion tube on a distal side of the shoulder portion.

7. The endoscope assembly of claim 5 wherein the sheath retaining member is a C-shaped member.

8. The endoscope assembly of claim 7 wherein the distal end portion of the insertion tube has a generally D-shaped cross-sectional area.

9. The endoscope assembly of claim 5 wherein the distal end portion of the insertion tube has a first portion with a first semi-circular outer surface, and a second portion with a second semi-circular outer surface, the first semi-circular outer surface having a first radius that is smaller than a second radius of the second semi-circular outer surface, the sheath retaining member being attached to the first semi-circular outer surface and being adjacent to the second semi-circular outer surface.

10. The endoscope assembly of claim 9 wherein the sheath retaining member has a third semi-circular outer surface with a third radius that is approximately the same as the second radius.

11. The endoscope assembly of claim 10 wherein the second distal end portion of the insertion tube has a generally D-shaped cross-sectional area and the sheath retaining member is a C-shaped member.

12. The endoscope assembly of claim 5 wherein the sheath retaining member is integrally connected to the distal end portion of the insertion tube.

13. A method of securing a sheath having a working channel extending therethrough on an insertion tube of an endoscope, the sheath being sized to receive the insertion tube therein, the insertion tube having a distal end portion with a pair of spaced-apart protruding sheath retaining tabs thereon, comprising the steps of:

radially expanding the sheath to an expanded position;

inserting the insertion tube into the sheath when in the expanded position and positioning the distal end portion of the insertion tube adjacent a distal end portion of the sheath;

moving the sheath from the expanded position to a contracted position after the distal end portion of the insertion tube is adjacent to the distal end portion of the sheath; and stretching a portion of the sheath over the sheath retaining tabs with the portion of the sheath tightly engaging the sheath retaining, tabs, the sheath retaining tabs retaining the distal end portion of the sheath adjacent the distal end portion of the insertion tube and preventing axial movement of the distal end portion of the sheath relative to the distal end portion of the insertion tube.

* * * * *